(12) United States Patent
Uchida et al.

(10) Patent No.: US 8,201,999 B2
(45) Date of Patent: Jun. 19, 2012

(54) RADIATION IMAGING APPARATUS

(75) Inventors: Mitsuaki Uchida, Kanagawa-ken (JP); Kenichi Kato, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 253 days.

(21) Appl. No.: 12/659,889

(22) Filed: Mar. 24, 2010

(65) Prior Publication Data

US 2010/0243924 A1    Sep. 30, 2010

(30) Foreign Application Priority Data

Mar. 27, 2009    (JP) ................. 2009-078080

(51) Int. Cl.
 *H05G 1/02*    (2006.01)
(52) U.S. Cl. ...................................... 378/197
(58) Field of Classification Search .................. 378/196, 378/197
 See application file for complete search history.

(56) References Cited

U.S. PATENT DOCUMENTS

| | | | | |
|---|---|---|---|---|
| 4,679,223 A | * | 7/1987 | Ohlson et al. | 378/197 |
| 5,740,227 A | * | 4/1998 | Kusch | 378/197 |
| 7,641,391 B2 | | 1/2010 | Schwieker | |
| 7,874,727 B2 | * | 1/2011 | Forster et al. | 378/197 |

FOREIGN PATENT DOCUMENTS

| | | |
|---|---|---|
| JP | 2000-316838 | 11/2000 |
| JP | 2007-244569 | 9/2007 |

* cited by examiner

*Primary Examiner* — Glen Kao
(74) *Attorney, Agent, or Firm* — Jean C. Edwards, Esq.; Edwards Neils PLLC

(57) ABSTRACT

A supporting/moving section for supporting and moving a device to predetermined positions at which radiation imaging is performed is prepared. An operating portion is provided for manipulating the movement of the device supported by the supporting/moving means. A detecting section outputs detection signals, which are obtained by detecting external forces which are applied to the operating portion. A control section controls the supporting/moving means to move the device such that the movement tracks target values for movement, which are determined from the detection signals. During manipulation of the operating portion, a unique oscillation frequency measuring section executes measurements to obtain a unique oscillation frequency of the device. A unique oscillation attenuating section attenuates signal components, which are included in control signals output by the control means to control the supporting/moving means and cause the movement of the device to fluctuate at the unique oscillation frequency, in real time.

12 Claims, 6 Drawing Sheets

RADIATION IMAGING APPARATUS

CROSS-REFERENCE TO RELATED APPLICATIONS

The present application claims priority from Japanese Patent Application No. 2009-078080, filed Mar. 27, 2009, the contents of which are herein incorporated by reference in their entirety.

BACKGROUND OF THE INVENTION

1. Field of the Invention

The present invention is related to a radiation imaging apparatus. More specifically, the present invention is related to a radiation imaging apparatus that moves a device to be employed in radiation images, by an operator manipulating an operating handle provided on the device.

2. Description of the Related Art

Conventionally, it is uncommon for small scale medical facilities, such as physicians in private practice and clinics, to install radiation imaging apparatuses dedicated to imaging specific portions of subjects. These medical facilities generally employ a single radiation imaging apparatus to perform radiation imaging of various body parts as necessary. For example, radiation imaging systems, in which an upright imaging table and a supine imaging table are installed in a single imaging room, a radiation source is supported by a ceiling runner suspension device or the like, and the irradiation direction of radiation is adjusted to be toward the upright imaging table and the supine imaging table by moving or changing the orientation of the radiation source, are known (refer to Japanese Unexamined Patent Publication No. 2007-244569 and U.S. Pat. No. 7,641,391).

The ceiling runner suspension device of such a known radiation imaging system is equipped with: a ceiling horizontal movement base that moves along the ceiling in the horizontal direction; and a telescoping support column, which is mounted on the underside of the ceiling horizontal movement base and is capable of extending and contracting in the vertical direction by telescopic motion. There are known radiation imaging systems in which a radiation source is mounted to the lower end of the telescoping support column.

There is also a known radiation imaging apparatus of the type described above, in which a operating handle is provided on a radiation source, external forces which are applied to the operating handle are detected, and the radiation source is moved by drive means, such as motors, according to the external forces to assist manual movement (to provide "power assistance") when moving the device (refer to Japanese Unexamined Patent Publication No. 2000-316838).

There are also known radiation imaging apparatuses having the power assistance function, in which a device is moved in the directions in which the external forces are applied at speeds corresponding to the magnitudes of the external forces.

Ceiling runner suspension devices which are designed for small scale medical facilities have comparatively low rigidity. In addition, radiation sources are provided at the lower ends of telescoping support columns that extend downward from ceiling horizontal movement bases. Therefore, there are cases in which the radiation sources sway like a pendulum at a specific oscillation frequency (unique oscillation frequency) corresponding to the supporting state of the ceiling runner suspension device. Further, there are cases in which the ceilings, on which the ceiling runner suspension devices are mounted, sway themselves. In these cases, the radiation sources sway by receiving the influence of the swaying ceilings as well.

The unique oscillation frequency, at which a radiation source oscillates, change according to the state of the ceiling on which a ceiling runner suspension device is provided, the rigidity of the ceiling runner suspension device, and the supporting state of the radiation source by the ceiling runner suspension device. The unique oscillation frequency varies according to the position of the ceiling runner suspension device along rails mounted on the ceiling (at the ends of the rails, and the center of the rails, etc.), the degree of expansion/contraction of a telescoping support column, and rotation (change of orientation) of the radiation source when changing from upright imaging to supine imaging, for example. Note that the oscillation frequency of the saying of the radiation source, which is supported by the ceiling runner suspension device, when the radiation source is caused to freely oscillate, is the unique oscillation frequency.

There are also cases in which that radiation source sways at the unique oscillation frequency when an operator urges an operating handle mounted thereon, to move the radiation source in the directions in which the urging force is applied at a speed corresponding to the magnitude of the external force, using the aforementioned power assistance function. In these cases, the urging force applied on the operating handle and the swaying of the radiation source at the unique oscillation frequency interfere with each other, and the force which is applied to the operating handle fluctuates periodically at the unique oscillation frequency.

If control of the power assistance function reacts to the fluctuations in the external force applied to the operating handle at the unique oscillation frequency, the swaying of the radiation source at the unique oscillation frequency is amplified, resulting in discomfort when operating the operating handle.

A possible measure that may be considered in order to suppress such swaying of the radiation source is to determine the frequency properties of the control of the power assistance function such that the control of the power assistance function does not react to the unique oscillation frequency of the sway of the radiation source (hereinafter, also referred to as "unique oscillation frequency of the oscillation of the radiation source") at all positions that the radiation source is moved to. That is, the control of the power assistance function that moves the radiation source may be set such that it does not react to the unique oscillation frequency of the oscillation of the radiation source at all positions.

However, if this measure is adopted, the frequency properties of the control of the power assistance function are determined such that the power assistance function does not react to the unique oscillation frequencies of the oscillation of the radiation source. Therefore, the control of the power assistance reaction will become slow to react. That is, the movement of the radiation source according to manipulation of the operating handle will become delayed, and the operability of the operating handle will deteriorate.

Note that it is acceptable for the radiation source to move while freely oscillating at its unique oscillation frequency when an operator is manipulating the operating handle. However, if the free oscillation (oscillation at the unique oscillation frequency) of the radiation source is amplified under control of the power assistance function and the amplitude becomes greater, this is a problem, because the operability of the operating handle will deteriorate.

For this reason, there is demand to enable movement of radiation sources without delays in control of a power assistance function with respect to manipulation of operating handles, and also without oscillations at the unique oscillation frequencies of the radiation sources being amplified under control of a power assistance function.

Note that the aforementioned problem is related to radiation sources or radiation detectors, which are devices that are movably supported and are employed to perform radiation imaging. This problem commonly occurs when the devices are moved such that the movement tracks target values for movement (such as movement direction and movement speed), which are determined according to external forces applied to operating handles.

SUMMARY OF THE INVENTION

The present invention has been developed in view of the foregoing circumstances. It is an object of the present invention to provide a radiation imaging apparatus which is capable of suppressing deterioration of the quality of operability when moving a device employed to perform radiation imaging.

A radiation imaging apparatus of the present invention comprises:

a supporting/moving means, for supporting a device, which is employed to perform radiation imaging, and for moving the device to predetermined positions at which radiation imaging is performed;

an operating portion provided on the device, for manipulating the movement of the device which is supported by the supporting/moving means;

detecting means, for detecting external forces which are applied to the operating portion, and outputs detection signals that represent the external forces; and control means, for controlling the supporting/moving means to move the device such that the movement tracks target values for movement, which are determined from the detection signals;

the radiation imaging apparatus being configured to move the device by manipulating the operating portion to apply external forces thereon, and is characterized by further comprising:

measuring means, for measuring a unique oscillation frequency that represents the oscillation of the device in a state in which the device is being supported by the supporting/moving means; and unique oscillation component attenuating means, for causing the measuring means to execute measurements of the unique oscillation frequency and for attenuating signal components, which are included in control signals output by the control means to control the supporting/moving means and cause the movement of the device to fluctuate at the unique oscillation frequency, in real time.

The operating handle may be of any configuration as long as it is formed such that external forces can be applied thereto to manipulate movement of the device. The operating handle is not limited to that having a portion that can be manually grasped, and may be of a configuration on which a hand may be placed, or of a configuration that can be simply pushed.

The unique oscillation frequency of the oscillation of the device changes corresponding to movement of the device by the supporting/moving means of the radiation imaging apparatus. Note that the unique oscillation frequency is an oscillation frequency of oscillation which is observed when the device is caused to oscillate freely in a state that it is supported by the supporting/moving means.

The target values for movement may be the direction in which the device is moved and the speed at which the device is moved.

A configuration may be adopted, wherein:

the detection signals output from the detecting means are input to the unique oscillation component attenuating means;

the unique oscillation component attenuating means corrects the detection signals by attenuating signal components included in the detection signals that represent fluctuations in the external forces which are applied to the operating portion at the unique oscillation frequency, and outputs the corrected detection signals.

A configuration may be adopted, wherein:

the supporting/moving means supports the device in a state in which it is suspended from the ceiling of a room. Further, the supporting/moving means may move the device in the vertical and horizontal directions.

The device may be one of a radiation source and a radiation detector.

A configuration may be adopted, wherein:

the detecting means detects the magnitudes and directions of the external forces which are applied to the operating portion, and outputs detection signals that represent the magnitudes and directions of the external forces; and the target values for movement of the device are determined such that the device is moved in the directions in which the external forces are applied at speeds corresponding to the magnitudes of the external forces.

A configuration may be adopted, wherein:

the unique oscillation component attenuating means attenuates the signal components employing a variable low pass filter or a variable band pass filter. A variable band pass filter is a filter that attenuates signals of specific frequencies, and passes signals having higher frequencies and lower frequencies than the specific frequencies.

The radiation imaging apparatus of the present invention is equipped with the measuring means, for measuring a unique oscillation frequency that represents the oscillation of the device in a state in which the device is being supported by the supporting/moving means; and the unique oscillation component attenuating means, for causing the measuring means to execute measurements of the unique oscillation frequency and for attenuating signal components included in control signals, which are output by the control means to control the supporting/moving means and cause the movement of the device to fluctuate at the unique oscillation frequency, in real time. Therefore, the oscillation of the device at the unique oscillation frequency being amplified under control of the control means can be suppressed. Thereby, deterioration of the operative quality when moving a device employed to perform radiation imaging can be suppressed.

That is, the unique oscillation component attenuating means can designate the unique oscillation frequency, which changes according to the movement of the device, as frequencies that the control for moving the device does not react to, in real time. Therefore, the range of frequencies that the control for moving the device does not react to need not be unnecessarily expanded, and amplification of the oscillation of the device at the unique oscillation frequency under the control of the control means can be suppressed. Thereby, it becomes possible to prevent delays in reaction time of the control means with respect to manipulation of the operating handle and also to prevent oscillation of the device at the unique oscillation frequency from being amplified during manipulation of the operating handle. Accordingly, deterioration in the quality of operability during movement of the device for performing radiation can be suppressed, and discomfort during manipulation of the operating handle can be eliminated.

A configuration may be adopted, wherein:
the detection signals output from the detecting means are input to the unique oscillation component attenuating means; the unique oscillation component attenuating means corrects the detection signals by attenuating signal components included in the detection signals that represent fluctuations in the external forces which are applied to the operating portion at the unique oscillation frequency, and outputs the corrected detection signals. In this case, it becomes possible to more positively prevent delays in reaction time of the control means with respect to manipulation of the operating handle and also to prevent oscillation of the device at the unique oscillation frequency from being amplified during manipulation of the operating handle. Accordingly, deterioration in the quality of operability during movement of the device for performing radiation can be suppressed.

A configuration may be adopted, wherein:
the supporting/moving means supports the device in a state in which it is suspended from the ceiling of a room, and moves the device in the vertical and horizontal directions. Because devices which are suspended from the ceilings of rooms are more likely to sway, the advantageous effects of preventing delays in reaction time of the control means with respect to manipulation of the operating handle and also preventing oscillation of the device at the unique oscillation frequency from being amplified during manipulation of the operating handle will become more conspicuous.

A configuration may be adopted, wherein:
the detecting means detects the magnitudes and directions of the external forces which are applied to the operating portion, and outputs detection signals that represent the magnitudes and directions of the external forces; and
the target values for movement of the device are determined such that the device is moved in the directions in which the external forces are applied at speeds corresponding to the magnitudes of the external forces. In this case, it becomes possible to more positively prevent delays in reaction time of the control means with respect to manipulation of the operating handle and also to prevent oscillation of the device at the unique oscillation frequency from being amplified during manipulation of the operating handle.

Note that a configuration may be adopted, wherein: the unique oscillation component attenuating means attenuates the signal components employing a variable low pass filter. In this case, it becomes possible to more positively prevent delays in reaction time of the control means with respect to manipulation of the operating handle and also to prevent oscillation of the device at the unique oscillation frequency from being amplified during manipulation of the operating handle.

Further, a configuration may be adopted, wherein: the unique oscillation component attenuating means attenuates the signal components employing a variable band pass filter. In this case, it becomes possible to prevent oscillation of the device at the unique oscillation frequency from being amplified during manipulation of the operating handle, without the range of frequencies that the control for moving the device does not react to being expanded unnecessarily.

DESCRIPTION OF THE PREFERRED EMBODIMENTS

Figure 1:
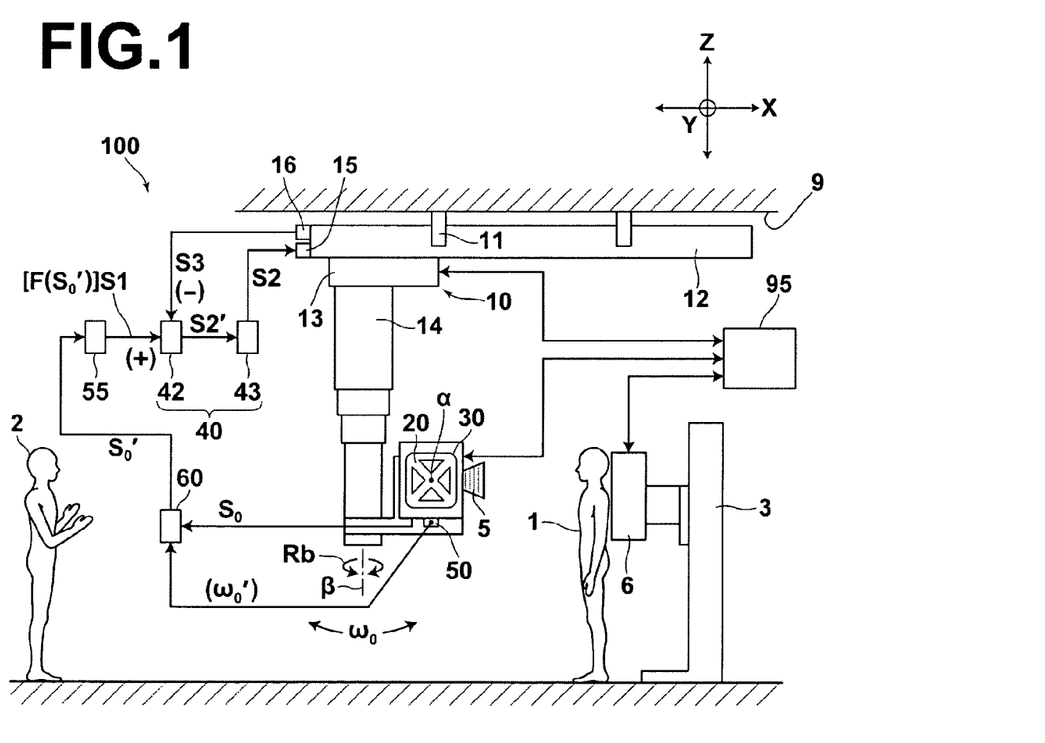
FIG. 1 is a side view that schematically illustrates the structure of a radiation imaging apparatus according to an embodiment of the present invention in the case that upright radiation imaging is to be performed.
Figure 2:
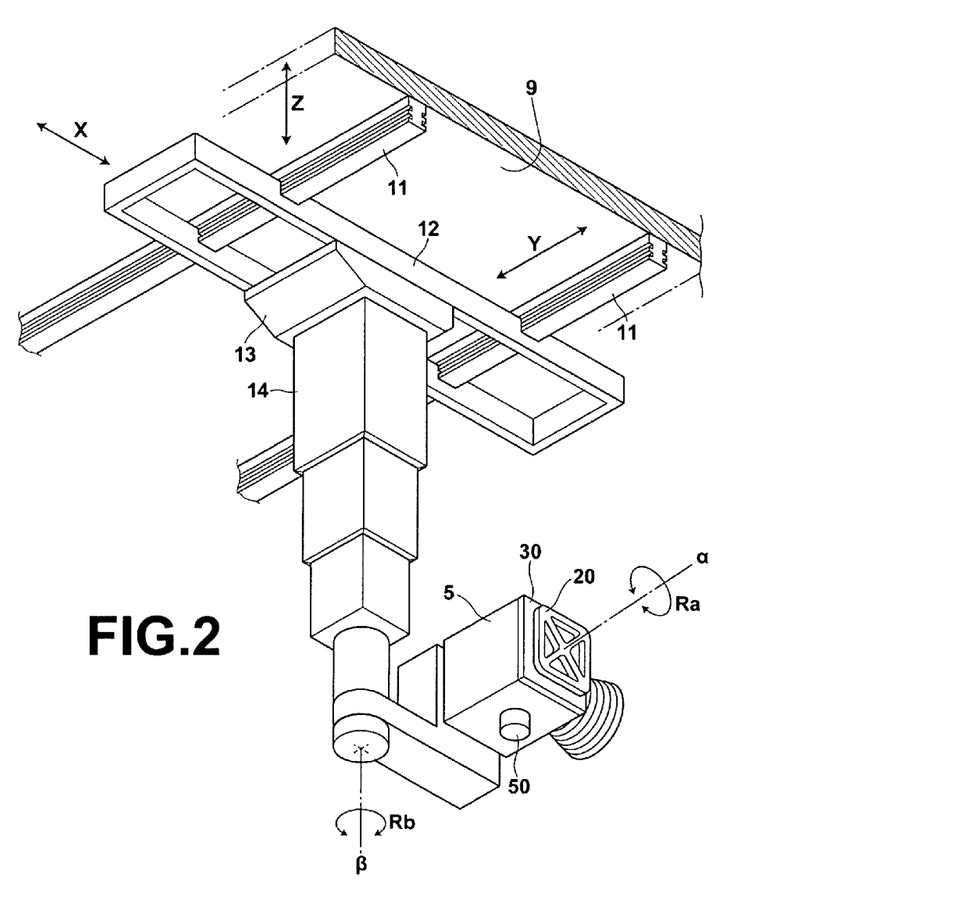
FIG. 2 is a magnified perspective view that illustrates the structure of a supporting/moving section.
Figure 3:
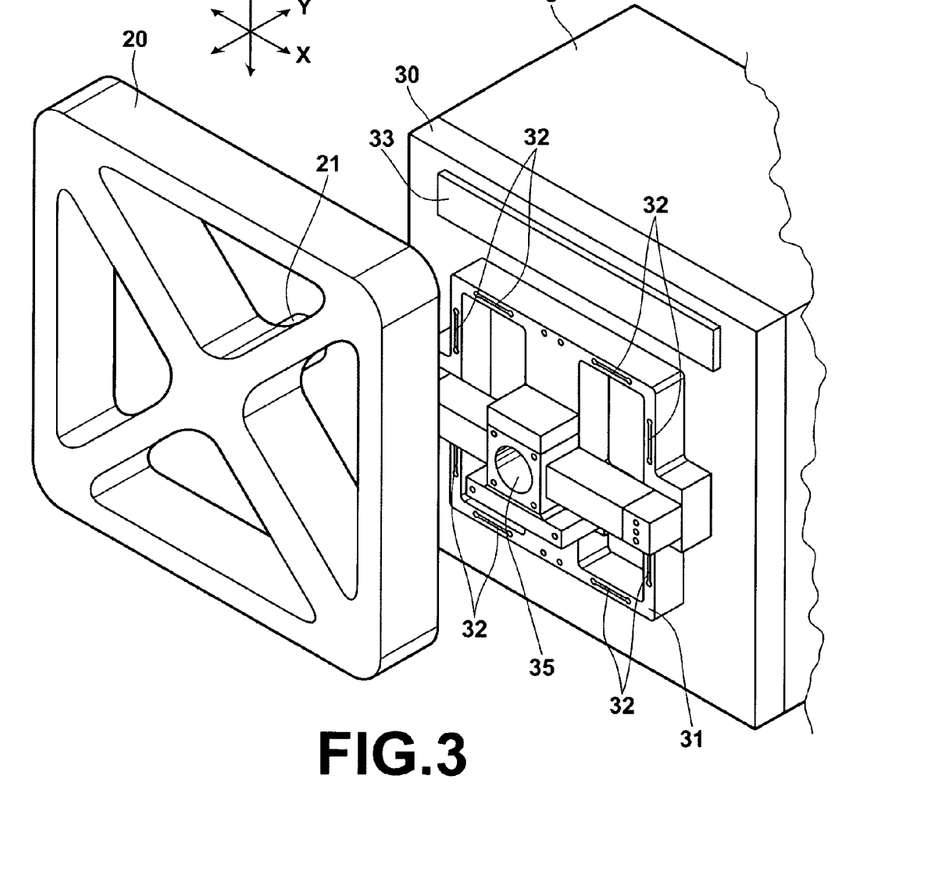
FIG. 3 is a magnified perspective view that illustrates the state in which an operating handle is mounted onto a radiation source via a detecting section.

Hereinafter, an embodiment of the present invention will be described with reference to the attached drawings. FIG. 1 is a side view that schematically illustrates the structure of a radiation imaging apparatus 100 according to an embodiment of the present invention in the case that upright radiation imaging is to be performed. FIG. 2 is a magnified perspective view that illustrates the structure of a supporting/moving section. FIG. 3 is a magnified perspective view that illustrates the state in which an operating handle is mounted onto a radiation source via a detecting section.

As illustrated in the drawings, the radiation imaging apparatus 100 is a radiation imaging apparatus which is suspended from the ceiling of a room. The radiation imaging apparatus 100 is equipped with: a radiation source 5, which is a device to be employed in radiation imaging; a radiation detector 6, for detecting radiation which is irradiated by the radiation source 5 and passes through a subject 1; a supporting/moving section 10, for moving the radiation source 5 in the vertical and horizontal directions while supporting the radiation source 5 in a state in which the device is suspended from the ceiling 9 of a room; an operating handle 20, which is integrally mounted onto the radiation source 5, for operating the movement of the radiation source 5 by the supporting/moving section 10; and a detecting section 30, for detecting external forces which are applied to the operating handle 20 and outputs signals So that indicate the magnitude and direction of the external forces. Note that the unique oscillation frequency of the radiation source 5 in a state in which it is being supported by the supporting/moving section 10 changes according to the movement of the radiation source 5 by the supporting/moving section 10.

The radiation imaging apparatus 100 is further equipped with: a unique oscillation frequency measuring section 50, for measuring the unique oscillation frequency $\omega_0$ of the radiation source 5 while it is in a state in which it is being supported by the supporting/moving section 10 in real time; and a unique oscillation component attenuating section 60, for attenuating signal components included in the detection signals So that represent fluctuations in the external forces which are applied to the operating handle at the unique oscillation frequency ωo, and outputs corrected detection signals So'.

The unique oscillation component attenuating section 60 attenuates signal components, which are included in control signals S2 for controlling the supporting/moving section 10 and cause the movement of the device to fluctuate at the unique oscillation frequency ωo, in real time.

Note that the unique oscillation frequency measuring section 50 may employ a method for measuring the unique oscillation frequency ωo by using acceleration sensors.

The radiation imaging apparatus is further equipped with: a target value setting section 55, into which the corrected detection signals So' are input, for determining target values for movement F(So') (movement direction and movement speed) according to external forces represented by the corrected detection signals So' in real time; and a control section 40 for controlling the supporting/moving means 10 to support the radiation source 5 such that the movement tracks the target values F(So') for movement.

The control section 40 controls the supporting/moving means 10 to move the radiation source 5 such that the movement tracks the target values F(So') for movement.

Thereby, the radiation source 5 can be moved by the controlling section 40 controlling the supporting/moving section 10 according to manipulations of the operating handle 20 by an operator.

Note that the unique oscillation frequency ωo is an oscillation frequency which is observed when the radiation source 5 is caused to oscillate freely in a state that it is supported by the supporting/moving means 10.

As illustrated in FIG. 2, the supporting/moving section 10 is equipped with fixed rails 11 which are provided on the ceiling 9; a movable rail 12 that extends in a direction perpendicular to the direction that the fixed rails 11 extend in, and is capable of moving in the direction that the fixed rails 11 extend in (the direction indicated by arrow Y in FIG. 2) while being suspended by the fixed rails 11; a horizontally moving base 13 which is capable of moving in the direction that the movable rail 11 extends in (the direction indicated by arrow X in FIG. 2) while being suspended by the movable rail 12; a telescoping support column 14 which is mounted to the horizontally moving base 13 and is capable of moving in the vertical direction (the direction indicated by arrow Z in FIG. 3) by telescopic motion; and drive motors (not shown) for driving the movable rail 12 in the Y direction, for driving the horizontally moving base 13 in the X direction, and for extending and contracting the telescoping support column 14.

Further, the supporting/moving section 10 is equipped with: an operation control section 15, into which the control signals S2 for moving the radiation source 5 output from the control section 40 are input, for driving the drive motors to drive the horizontally moving base 13 in the X direction, and to extend and contract the telescoping support column 14 according to the control signals S2; and an operation measuring section 16, for measuring the movement (movement direction and movement speed) of the radiation source 5.

Note that the measurements preformed by the operation measuring section 16 may be performed by known linear encoders, laser measuring devices, potentiometers, or the like.

As illustrated in FIGS. 1 and 2, the radiation source 5 is mounted to the lower end of the telescoping support column 14. The radiation source 5 is capable of changing its orientation with respect to the telescoping support column 14 in order to enable both upright radiation imaging and supine radiation imaging.

More specifically, the radiation source 5 is mounted on the telescoping support column 14 so as to be rotatable about a horizontal axis α (in the directions indicated by arrow Ra of FIG. 2), which is perpendicular to the Z axis direction. In addition, the radiation source 5 is rotatable about a vertical axis β (in the directions indicated by arrow Rb of FIG. 2), which is parallel to the central axis that extends in the extending/contracting direction of the telescoping support column 14 and also parallel to the Z axis.

Note that in FIGS. 1 and 2, the orientation of the radiation source 5 is set such that radiation is irradiated in the X axis direction.

Here, the operating handle 20 is integrally mounted onto the radiation source 5 via the detecting section 30. The detecting section 30 detects the magnitude and direction of external forces which are applied to the operating handle 20. The detecting section 30 detects forces which are applied in each of the X direction, the Y direction, and the Z direction, or forces (rotational moments) applied about the X direction axis, the Y direction axis, and the Z direction axis, to detect the direction and magnitude of external forces which are applied to the operating handle 20.

As illustrated in FIG. 3, the operating handle 20 is mounted to the radiation source 5 via the hardware portion 31 of the detecting section 30. That is, the four corners of the hardware portion 31 are fixed on the radiation source 5, and the operating handle 20 is fixed to the hardware portion 31 by a shaft 21 that protrudes from the operating handle 20 engaging with an opening 35 provided in the center of the hardware portion 31, to mount the operating handle 20 to the radiation source 5 via the hardware portion 31.

When external forces are applied to the operating handle 20, detecting regions 32 of the hardware portion 31, which have been processed to be easily strained, become strained. The strains of the detecting regions 32 are detected by strain gauges (not shown) which are mounted to each of the detecting regions 32. The outputs of the strain gauge of each of the detecting regions 32 are input to a circuit board 33, which is a software portion of the detecting section 30. The circuit board 33 receives input of the strain values detected by the strain gauges of the detecting regions 32, derives the magnitude and direction of the external forces which are applied to the operating handle 20, and outputs these values as the detection signals So.

The control section 40 is equipped with: a comparing section 42, for comparing feedback signals S3 that represent the movement (movement direction and movement speed) of the radiation source 5, obtained by the operation measuring section 16 and the target values F(So') determined by the target value setting section 55, and outputs difference signals S2' that represent the differences therebetween; and a control signal generating section 43, for converting the difference signals S2' output from the comparing section 42 to signals that represent the amounts of movement (movement direction and movement speed) of the radiation source 5, and outputs control signals S2 that represent the amounts of movement obtained by the conversion.

More specifically, the control section 40 controls the supporting/moving section 10 such that the movement direction and the movement speed that the feedback signals S3 represent match the target values F(So') determined by the target value setting section 55, that is, such that the movement of the radiation source 5 by the supporting/moving section 10 tracks the target values F(So') for movement of the radiation source 5.

As described above, the target value setting section 55 sets the directions of the external forces applied to the operating handle 20 as target values, and also sets speeds corresponding to the magnitudes of the external forces applied to the operating handle 20 as target values.

Note that the unique oscillation component attenuating section 60 may employ a variable low pass filter or a variable band pass filter. A variable lowpass filter attenuates signal components that represent fluctuations in the external forces having frequencies of a predetermined value or less, and passes signal components that represent fluctuations in the external forces having frequencies greater than the predetermined value. A variable band pass filter is a filter that attenuates signal components that represent fluctuations in the external forces of specific frequencies, and passes signal components that represent fluctuations in the external forces having higher frequencies and lower frequencies than the specific frequencies.

<Operation During Radiation Imaging>

Next, an operation in which the radiation imaging apparatus 100 of the present embodiment is employed to perform upright radiation imaging will be described.

The operator 2 who executes upright radiation imaging prompts the subject 1 to stand toward the front surface of the radiation detector 6, which is supported by an upright imaging base 3.

Next, the operator 2 grips the operating handle 20, which is provided integrally with the radiation source 5, and applies external force to the handle 20 in the direction that the radiation source 5 is to be moved.

The magnitude and the direction of the external force which is applied to the operating handle 20 are detected by the detecting section 30. Detection signals So that indicate the magnitude and the direction of the external force are output by the detecting section 30.

The detection signals So output from the detecting section 30 and signals that represent the unique oscillation frequency ωo of the radiation source 5 while it is in a state in which it is being supported by the supporting/moving section 10 measured by the uocms 50 are input to the unique oscillation component attenuating section 60.

The unique oscillation component attenuating section 60 attenuates signal components included in the detection signals So that represent fluctuations in the external forces which are applied to the operating handle 20 at the unique oscillation frequency ωo in real time, and outputs corrected detection signals So'. That is, the unique oscillation component attenuating section 60 attenuates signal components that represent fluctuations in the direction and magnitude of the external forces applied to the operating handle 20 at the unique oscillation frequency ωo, and outputs the corrected detection signals So', which are the detection signals So corrected such that these signal components are attenuated.

The corrected detection signals So' output from the unique oscillation component attenuating section 60 are input to the target value setting section 55. The target value setting section 5 determines target values for movement F(So') (movement direction and movement speed) according to external forces represented by the corrected detection signals So' in real time.

Target value signals S1 output from the target value setting section 55 and feedback signals S3 output from the operation measuring section 16 are input to the comparing section 42, and the comparing section 42 outputs difference signals S2' that represent the difference between the two.

The control signal generating section 43 converts the input signals S2' to signals that represent movement amounts of the radiation source 5 constituted by the magnitudes of vectors that indicate movement directions and the magnitudes of vectors that indicate movement speeds, for example, and outputs these signals as control signals S2. Alternatively, the input signals S2' are converted to signals that represent each of the vectors, such as a movement speed of 0.3 m/sec in the X direction, a movement speed of 0.2 m/sec in the Y direction, and a movement speed of 0.1 m/sec in the Z direction, then outputs these signals as the control signals S2.

The operation control section 15 of the supporting/moving section 10 moves the radiation source 5 such that the movement tracks the movement amounts represented by the control signals S2. That is, the operation control section 15 drives each of the drive motors, to move the horizontally moving base 13, and to extend and contract the telescoping support column 14.

The operation measuring section 16 of the supporting/moving section 10 measures the movement (the movement direction and the movement speed) of the radiation source 5, and outputs feedback signals S3 that indicate the movement (the movement direction and the movement speed) of the radiation source 5. The feedback signals S3 output from the operation measuring section 16 are input to the comparing section 42.

Feedback control is performed in this manner such that the actual movement of the radiation source 5 tracks target values for movement, which are determined by external forces applied to the operating handle 20.

Thereby, the operator 2 can move the radiation source 5 to a desired position, by manipulating the operating handle 20.

When radiation imaging is to be performed, the radiation source 5, the radiation detector 6, and the subject 1 are placed at predetermined positions. Then, the operator 2 inputs commands to execute radiation imaging to each component via a controller 95. Thereby, radiation Xe, which is emitted from the radiation source 5, passes through the subject 1 and is detected by the radiation detector 6.

The radiation detector 6 outputs image signals that represent a radiation image of the subject 1, which is detected by the radiation detector 6, and radiation imaging using the radiation imaging apparatus 100 is completed.

<Operation for Suppressing Oscillation of the Radiation Source at the Unique Oscillation Frequency>

Hereinafter, an operation for suppressing oscillation of the radiation source 5 at the unique oscillation frequency will be described.

Because the radiation imaging apparatus 100 is not a perfectly rigid body, the radiation source 5, which has a mass of 250 kg, sways when the horizontal moving base 13 is moved and when the telescoping support column 14 is extended and contracted.

The amplitude of the swaying of the radiation source 5 increases when the telescoping support column 14 is extended, when the radiation source 5 is positioned at the ends of the movable rails 12, and the like. In addition, in the case that the rigidity of the ceiling is low and the entirety of the supporting/moving section 10 is held in a state in which it is suspended from the ceiling, the radiation source 5 may sway corresponding to swaying of the ceiling.

The period of the oscillation of the radiation source 5, that is, the unique oscillation frequency ωo, varies according to the degree of extension of the telescoping support column 14, the position of the radiation source 5 with respect to the movable rails 12 and the fixed rails 11, the rigidity of the ceiling on which the supporting/moving section 10 is mounted, the orientation of the radiation source 5, and the like.

Here, when the operator 2 urges the operating handle 20 in a first direction, a speed V1 corresponding to the external force applied to the operating handle 20 becomes the target value for movement speed. Feedback control is administered with movement at the speed V1 in the first direction as the target value. Here, the properties of the feedback control are adjusted such that the amount of time until the radiation source 5 reaches the speed V1 is as short as possible, and such that overshooting of the target value is not repeated, that is, such that oscillating variations in the movement speed are not repeated to gradually approach the target value.

With regard to the radiation imaging apparatus 100, in which the feedback control properties are adjusted in this manner, the amount of discomfort experienced when an operator 2 manipulates the operating handle 20 should be small. However, discomfort is felt in the case that oscillation of the radiation source 5 at the unique oscillation frequency is amplified by such control.

That is, feedback control should be administered such that the radiation source 5 moves in the first direction at the speed V1 corresponding to the external force applied to the operating handle 20. However, if the radiation source 5 sways while the operator 2 is urging the operating handle 20 in the first direction, the external force applied to the operating handle 20 by the operator 2 fluctuates.

More specifically, even if the operator 2 attempts to apply a constant urging force to the operating handle 20 in the first direction, the force applied thereto decreases when the operating handle 20 is swaying toward the first direction (the direction in which the urging force is being applied), and increases when the operating handle 20 is swaying in a direction opposite the first direction (a direction opposite the direction in which the urging force is being applied).

For example, in the case that the unique oscillation frequency ωo when the radiation source 5 sways is 1 Hz, the external force applied to the operating handle 20 fluctuates at a period corresponding to 1 Hz when the operator 2 attempts to urge the operating handle 20 at a constant force in the first direction.

The external forces, which are applied to the operating handle 20, correspond to target values employed for feedback control. Therefore, the target values employed for feedback control also fluctuate at a period corresponding to 1 Hz.

That is, the operation of the feedback control, in which the target values that fluctuate at the period corresponding to 1 Hz are input, results in the supporting/moving section 10 moving the radiation source 5 at a movement speed that fluctuates at 1 Hz.

The movement speed of the operating handle 20, which is provided on the radiation source 5, fluctuates at 1 Hz in the same manner as the fluctuation in movement speed of the radiation source 5 at 1 Hz. Accordingly, the swaying at the unique oscillation frequency (1 Hz) of the operating handle 20 (radiation source 5) is amplified, and discomfort is experienced while the operator 2 manipulates the operating handle 20.

However, such fluctuations in the movement speed of the operating handle 20 (radiation source 5) are reduced by the operation of the unique oscillation component attenuating section 60.

That is, the unique oscillation frequency measuring section 50 measures the unique oscillation frequency ωo of the radiation source 5 while it is in a state in which it is being supported by the supporting/moving section 10 in real time. Then, the detection signals So output from the detecting section 30 and signals that represent the unique oscillation frequency ωo are input to the unique oscillation component attenuating section 60. The unique oscillation component attenuating section 60 generates corrected detection signals So', in which signal components included in the detection signals So that represent fluctuations in the external forces (the magnitudes and directions of the external forces) which are applied to the operating handle 20 at the unique oscillation frequency ωo are attenuated in real time, and outputs the corrected detection signals So' to the target value setting section 55.

The target value setting section 5 determines target values for movement F(So') (movement direction and movement speed) employing the corrected detection signals So', from which signal components that fluctuate at the unique oscillation frequency ωo have been removed.

Thereafter, the control section controls the supporting/moving section 10 such that the movement of the radiation source 5 by the supporting/moving section 10 tracks the target values F(So').

Thereby, the operation for moving the radiation source 5 employing the operating handle 20 will not react to external forces that fluctuate at the unique oscillation frequency ωo (1 Hz). Accordingly, control of the movement of the radiation source 5 will not be executed in a manner that fluctuates at a period of the unique oscillation frequency ωo (1 Hz), even if external forces are applied to the operating handle 20 at the period of the unique oscillation frequency ωo (1 Hz).

Note that here, a case has been described in which the unique oscillation component attenuating section 60 completely removes the signal components that represent the fluctuations of the external forces (the magnitudes and directions of the external forces), which are applied to the operating handle 20 at the unique oscillation frequency ωo, from the detection signals So detected by the detecting section 30. However, the present invention is not limited to a configuration in which signal components that represent the fluctuations of the external forces, which are applied to the operating handle 20 at the unique oscillation frequency ωo, are completely removed from the detection signals So. Advantageous effects similar to those obtained in the case that the signal components that represent the fluctuations of the external forces, which are applied to the operating handle 20 at the unique oscillation frequency ωo, are completely removed can also be obtained in cases that the signal components are partially removed.

Figure 4:
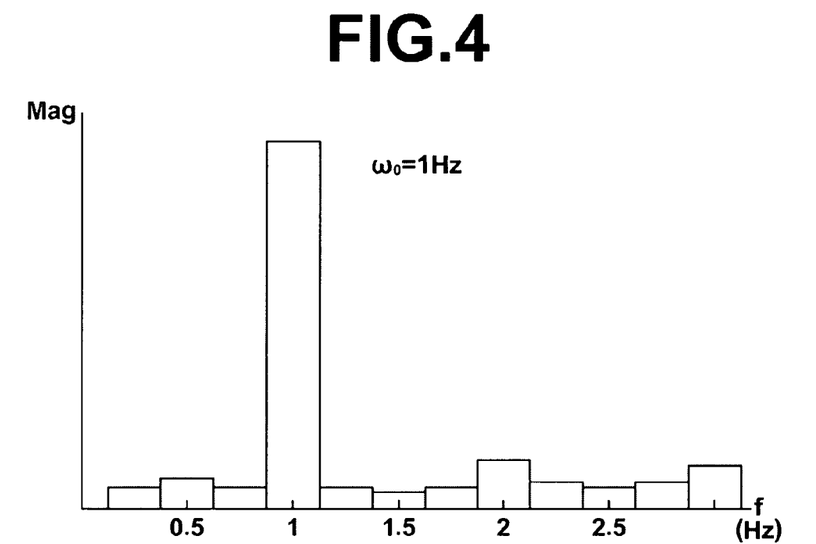
FIG. 4 is a graph that illustrates how signals detected by an acceleration sensor are analyzed by an FFT analyzer to, derive unique oscillation frequencies.
Figure 5:
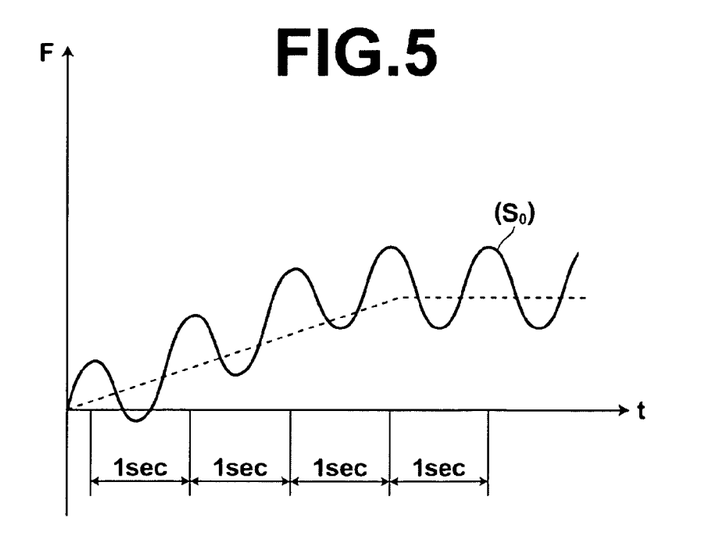
FIG. 5 is a graph that illustrates external forces applied by an operator combined with external forces, which are added due to the influence of the unique oscillation frequency of a radiation source.
Figure 6:
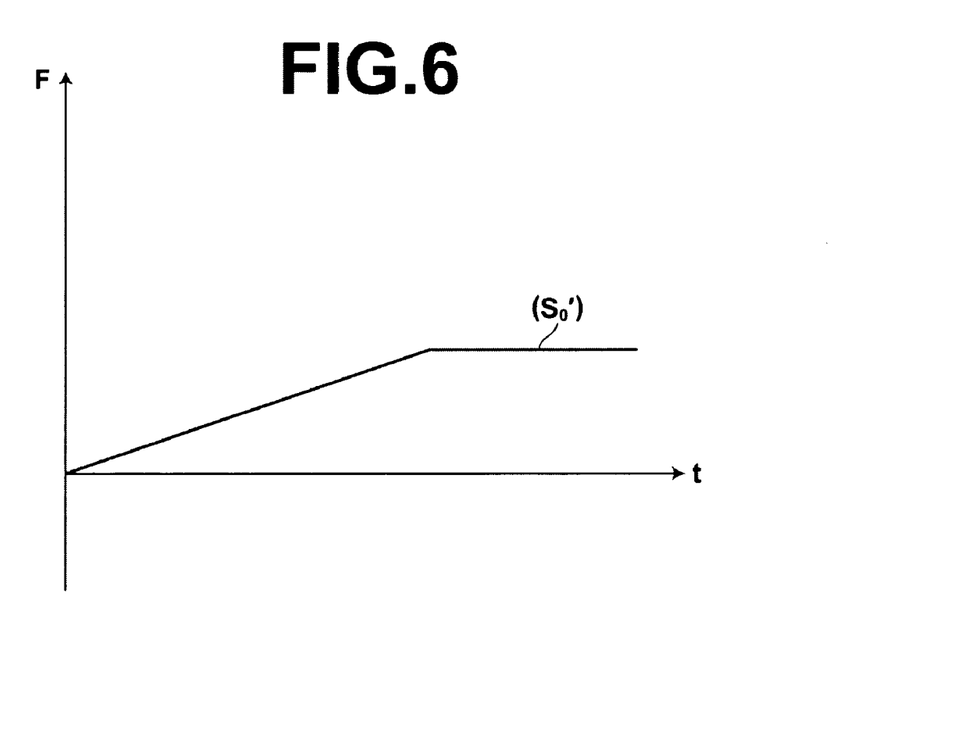
FIG. 6 is a graph that illustrates the external forces of FIG. 5, from which the external forces due to the influence of the unique oscillation frequency of the radiation source are removed.

FIG. 4 is a graph having a coordinate system in which the horizontal axis f represents frequencies and the vertical axis Mag represents the magnitudes of signals that illustrates the results of analysis of the movements of the radiation source 5 as it freely oscillated. More specifically, FIG. 4 is a graph that represents the results of analysis by an FFT analyzer of degrees of acceleration detected by an acceleration sensor fixed on the radiation source 5 as it freely oscillated. FIGS. 5 and 6 are graphs having a coordinate system in which the horizontal axis t represents time and the vertical axis F represents magnitudes of force, that illustrate external forces applied to the operating handle. FIG. 5 is a graph that illustrates external forces applied by an operator combined with external forces, which are added due to the influence of the unique oscillation frequency of the radiation source. FIG. 6 is a graph that illustrates the external forces of FIG. 5, from which the external forces due to the influence of the unique oscillation frequency of the radiation source are removed. That is, FIG. 6 is a graph that illustrates only the external forces applied to the operating handle by the operator.

Figure 7:
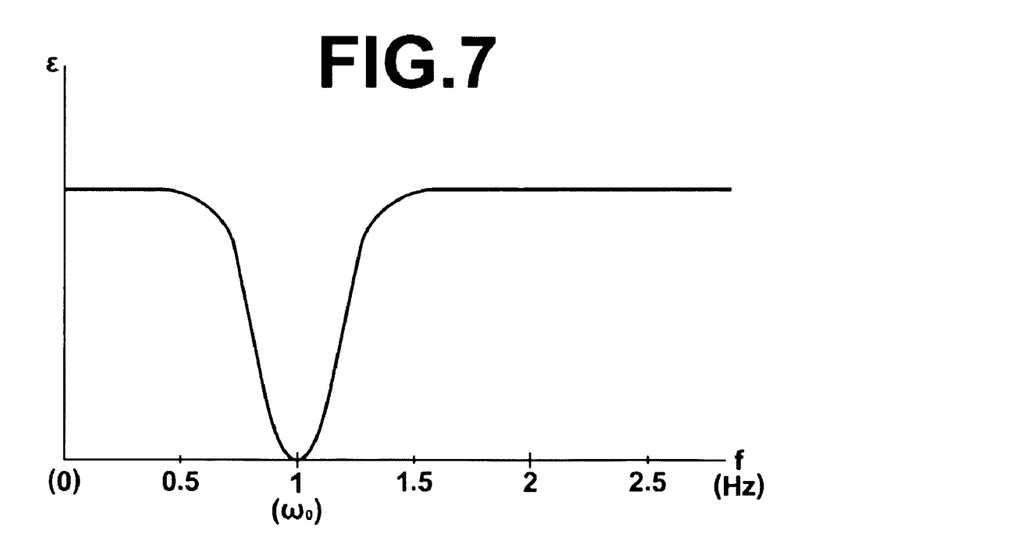
FIG. 7 is a graph that illustrates the filter properties of a band pass filter that only blocks oscillations of 1 Hz.
Figure 8:
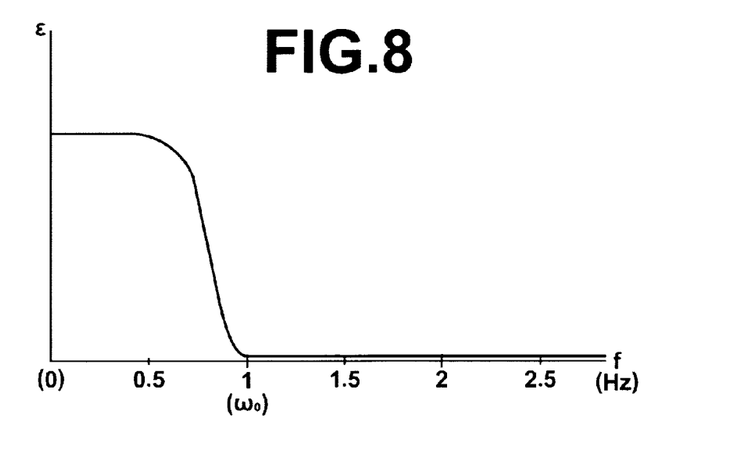
FIG. 8 is a graph that illustrates the filter properties of a low pass filter that blocks oscillations of 1 Hz and greater, while allowing oscillations of less than 1 Hz to pass therethrough.

In addition, FIGS. 7 and 8 are graphs having a coordinate system in which the horizontal axis f represents frequencies and the vertical axis ε represents transmissive rates, that illustrate filter properties of the unique oscillation component attenuating section. FIG. 7 is a graph that illustrates the filter properties of a band pass filter that only blocks oscillations of 1 Hz. FIG. 8 is a graph that illustrates the filter properties of a low pass filter that blocks oscillations of 1 Hz and greater, while allowing oscillations of less than 1 Hz to pass therethrough.

As illustrated in FIG. 4, the unique oscillation frequency measuring section 50 analyzes the manner in which the radiation source 5 oscillates with the FFT analyzer, to derive the unique oscillation frequency ωo. Note it is necessary for the supporting/moving section 10 to be oscillating in order to measure the unique oscillation frequency ωo. For this reason, the unique oscillation frequency measuring section 50 is placed in a state such that it is capable of measuring the unique oscillation frequency ωo at any time while the radiation imaging apparatus 100 is being operated. Then, the unique oscillation frequency measuring section 50 measures the oscillations of the radiation source 5 that occur during movement thereof by the supporting/moving section 10 and after the movement thereof, to derive the unique oscillation frequency ωo. Thereby, the unique oscillation frequency ωo can be measured without imparting shock onto the supporting/moving section 10 with an impulse hammer or the like.

As illustrated in FIG. 4, the unique oscillation frequency that represents the oscillation of the radiation source 5 while it is being supported by the supporting/moving section 10 as measured by the unique oscillation frequency measuring section 50 is 1 Hz.

The detection signals So output from the detecting section 30, which has detected magnitudes of force which are combinations of the urging forces in the first direction applied by the operator 2 combined with external forces, which are added due to the oscillation of the radiation source 5 at the unique oscillation frequency (1 Hz) are illustrated in the graph of FIG. 5. These detection signals So indicate that the unique oscillation frequency ωo of the radiation source 5 remains constant at 1 Hz during application of the urging force, and that the magnitude of the external force gradually increases while fluctuating at a period of 1 Hz.

When these detection signals So are processed by the unique oscillation component attenuating section 60 to remove the 1 Hz oscillating components, they become the corrected detection signals So' as illustrated in FIG. 6. The corrected detection signals So' representing only the components that indicate that the magnitude of the external force gradually increases are input to the target value setting section 55.

In this manner, the unique oscillation component attenuating section 60 causes the detecting section 30 to execute measurements of the unique oscillation frequency ωo during manipulation to apply external force to the operating handle 20 and attenuates the signal components included in control signals, which are output by the control section 40 to control the supporting/moving means 10, that cause the movement of the device to fluctuate at the unique oscillation frequency ωo in real time.

More specifically, it is desirable for the unique oscillation component attenuating section 60 to have properties such that only the unique oscillation frequency ωo (here, ωo=1 Hz) measured by the detecting section 30 is removed, as illustrated in FIG. 7. Alternatively, the unique oscillation component attenuating section 60 may have properties such that oscillating components having frequencies greater than or equal to the unique oscillation frequency ωo (here, ωo=1 Hz) are removed, while oscillating components having frequencies less than the unique oscillation frequency ωo (here, ωo=1 Hz) are maintained, as illustrated in FIG. 8.

The response characteristics of control for moving the radiation source 5 can be improved in the case that the unique oscillation component attenuating section 60 is of the type that removes only the unique oscillation frequency ωo measured by the detecting section 30 than in the case that the unique oscillation component attenuating section 60 is of the type that removes oscillating components having frequencies greater than or equal to the unique oscillation frequency ωo and maintains oscillating components having frequencies less than the unique oscillation frequency ωo. Therefore, tracking of the movement (movement direction and movement speed) of the radiation source 5 to the target values can be executed more smoothly.

That is, control to move the radiation source 5 such that the movement thereof tracks target values can be executed more smoothly. In other words, control can be executed such that the amount of time until the target values are reached do not become long, and such that oscillating variations in the movement are not repeated to gradually approach the target values. Therefore, the range of frequencies that the control for moving the device does not react to need not be unnecessarily expanded, and amplification of the oscillation of the device at the unique oscillation frequency under the control of the control means can be suppressed. Thereby, it becomes possible to prevent delays in reaction time of the control means with respect to manipulation of the operating handle and also to prevent oscillation of the device at the unique oscillation frequency from being amplified during manipulation of the operating handle.

Further, the oscillation (unique oscillation frequency) of the radiation source 5 while being supported by the supporting/moving section 10 may change due to movement of the radiation source 5 in the X, Y, and Z directions. Even in this case, however, the unique oscillation frequency measuring section 50 measures the unique oscillation frequency in real time, and the unique oscillation component attenuating section 60 removes signal components that represent fluctuations in applied external forces at the unique oscillation frequency from the detection signals output from the detecting section 30 in the same manner as described above. Thereby, it becomes possible to prevent delays in reaction time of the control means with respect to manipulation of the operating handle and also to prevent oscillation of the device at the unique oscillation frequency from being amplified during manipulation of the operating handle, regardless of where the radiation source 5 is moved to.

<Modification to the Radiation Imaging Apparatus>

Figure 9:
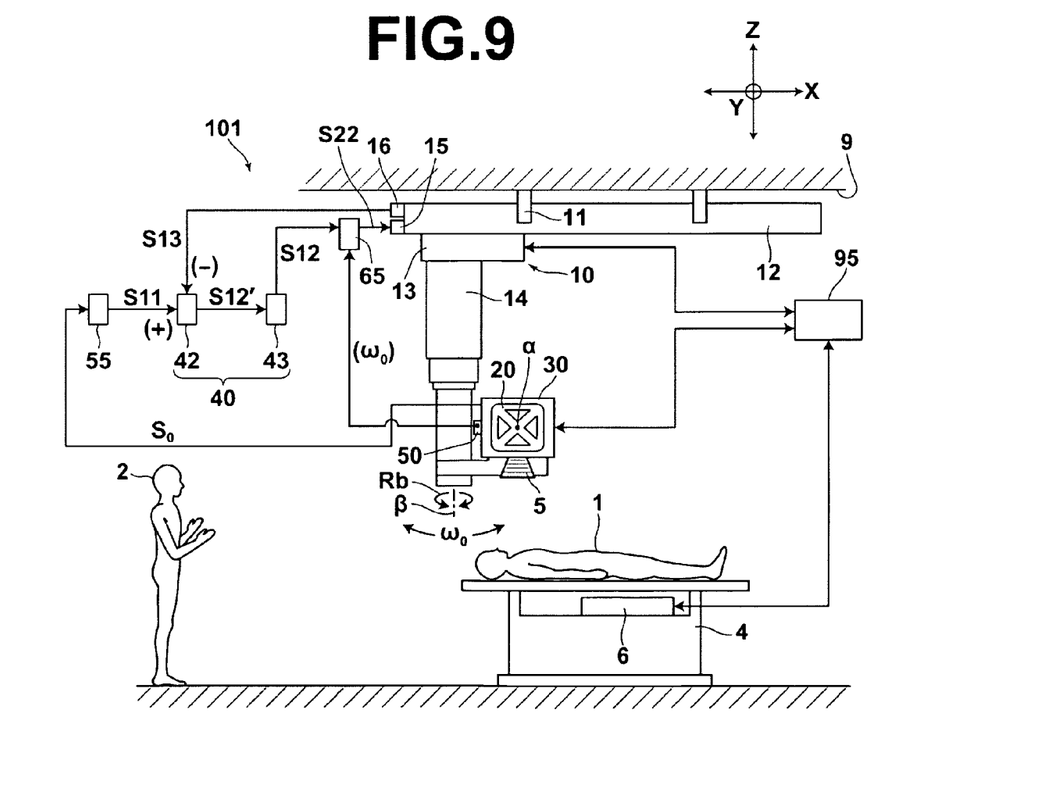
FIG. 9 is a side view that schematically illustrates the structure of a radiation imaging apparatus according to a modified embodiment of the present invention in the case that supine radiation imaging is to be performed.

FIG. 9 is a side view that schematically illustrates the structure of a radiation imaging apparatus 101 according to a modified embodiment of the present invention in the case that supine radiation imaging is to be performed.

In the radiation imaging apparatus 100 for performing upright radiation imaging described previously, the unique oscillation component attenuating section 60 attenuated signal components included in the detection signals So output from the detecting section 30 that represent fluctuations in the external forces applied to the operating handle 20 at the unique oscillation frequency ωo, to suppress amplification of the oscillation of the radiation source 5 at the unique oscillation frequency.

On the other hand, the radiation imaging apparatus 101 according to the modified embodiment illustrated in FIG. 9 performs supine radiation imaging, and the operator 2 places the subject toward the upper surface of the radiation detector 6, which is supported by a supine imaging base 4. Further, the operator 2 rotates the radiation source 5 about the horizontal axis α and about the vertical axis β, to set the orientation of the radiation source 5 such that radiation output therefrom is irradiated toward the subject 1 and the radiation detector 6.

Note that FIG. 9 illustrates a state in which the orientation of the radiation source 5 is set such that radiation is irradiated in the Z axis direction.

The radiation imaging apparatus 101 is equipped with a unique oscillation component attenuating section 65, for attenuating signal components, which are included in control signals S12 output from the control section 40 to control the supporting/moving section 10 and cause movement of the radiation source 5 supporting/moving section 10 to fluctuate at the unique oscillation frequency, in real time. Note that the radiation imaging apparatus 101 is not quipped with the unique oscillation component attenuating section 60 which was provided in the radiation imaging apparatus 100.

The other elements of the radiation imaging apparatus 101 are the same as those of the radiation imaging apparatus 100, which were described previously. Therefore, these elements will be denoted by the same reference numerals, and detailed descriptions thereof will be omitted.

Note that the signal components that cause the radiation source 5 to oscillate at the unique oscillation frequency are signal components, which are included in the control signals S12 and cause the supporting/moving section 10 to execute movement of the radiation source 5 in such a manner that the movement direction thereof and the movement speed thereof fluctuate at the unique oscillation frequency.

In the radiation imaging apparatus 101 of the modified embodiment, the detection signals So detected by the detecting section 30 are input to the target value setting section 55 as they are. The target value setting section 55 generates target value signals S11 that include the fluctuations at the unique oscillation frequency ωo, and outputs the target value signals S11.

The target value signals S11 output from the target value setting section 55 and feedback signals S3 output from the operation measuring section 16 are input to the comparing section 42, and the comparing section 42 outputs difference signals S12' that represent the difference between the two.

The control signal generating section 43 converts the input signals S12' to signals that represent movement amounts (movement direction and movement speed) of the radiation source 5, and outputs these signals as control signals S12.

The control signals S12 output from the control section 40 are input to the unique oscillation component attenuating section 65 prior to being input into the supporting/moving section 10. Thereby, signal components, which are included in the control signals S12 and cause fluctuations in the movement of the radiation source 5 at the unique oscillation frequency ωo, can be attenuated or removed.

That is, the unique oscillation component attenuating section 65 attenuates or removes the signal components, which are included in the control signals S12 and cause fluctuations in the movement of the radiation source 5 at the unique oscillation frequency ωo, to generate corrected control signals S22, and outputs the corrected control signals S22.

The corrected control signals S22 output from the unique oscillation component attenuating section 65 are input to the operation control section 15 of the supporting/moving section 10. The supporting/moving section 10 moves the radiation source 5 according to the corrected control signals S22.

Thereby, the operation of the supporting/moving section 10 to move the radiation source 5 can be set so as not to react to or to dull reactions with respect to the unique oscillation frequency. Accordingly, delays in reaction time of control with respect to manipulation of the operating handle can be prevented, and at the same time, oscillation of the radiation source at the unique oscillation frequency from being amplified under the control for moving the radiation source can be prevented.

Note that the other operations, advantageous effects, and the like of the radiation imaging apparatus 101 that employs the unique oscillation component attenuating section 65 are the same as those described with reference to the radiation imaging apparatus 100.

Embodiments have been described, in which the movement of the radiation source 5 was controlled. The present invention may also be applied to cases in which movement of the radiation detector 6 is controlled.

In addition, embodiments have been described, in which the movement of the radiation source 5 was performed under feedback control. The present invention may also be applied to cases in which the movement of the radiation source 5 is performed under open loop control, and further to cases in which the movement of the radiation source 5 is turned ON and OFF by manipulating the operating handle.

Note that in the embodiments described above, the target values for movement of the device, which are determined based on detection signals, were target values regarding movement directions and target values regarding movement speeds. However, the present invention is not limited to such a configuration, and any value may be employed as the target value. For example, the degree of acceleration during movement may be a target value, an angular speed may be designated as a target value in the case that the device is rotated.

Note that the measurement of the unique oscillation frequency performed by the detecting section may be performed only during movement of the device by the sm/s, only when the device is still, and both during movement of the device and when the device is still.

As described above, the present invention enables a device to be moved while suppressing oscillations of the device from being amplified at the unique oscillation frequency, without the operability of the operating handle deteriorating.

What is claimed is:

1. A radiation imaging apparatus, comprising:
   a supporting/moving means, for supporting a device, which is employed to perform radiation imaging, and for moving the device to predetermined positions at which radiation imaging is performed;
   an operating portion provided on the device, for manipulating the movement of the device which is supported by the supporting/moving means;
   detecting means, for detecting external forces which are applied to the operating portion, and outputs detection signals that represent the external forces; and
   control means, for controlling the supporting/moving means to move the device such that the movement tracks target values for movement, which are determined from the detection signals;
   the radiation imaging apparatus being configured to move the device by manipulating the operating portion to apply external forces thereon, and further comprising:
   measuring means, for measuring a unique oscillation frequency that represents the oscillation of the device in a state in which the device is being supported by the supporting/moving means; and
   unique oscillation component attenuating means, for causing the measuring means to execute measurements of the unique oscillation frequency and for attenuating signal components, which are included in control signals output by the control means to control the supporting/moving means and cause the movement of the device to fluctuate at the unique oscillation frequency, in real time.

2. A radiation imaging apparatus as defined in claim 1, wherein:
- the detection signals output from the detecting means are input to the unique oscillation component attenuating means;
- the unique oscillation component attenuating means corrects the detection signals by attenuating signal components included in the detection signals that represent fluctuations in the external forces which are applied to the operating portion at the unique oscillation frequency, and outputs the corrected detection signals.

3. A radiation imaging apparatus as defined in claim 1, wherein:
- the supporting/moving means supports the device in a state in which it is suspended from the ceiling of a room, and moves the device in vertical and horizontal directions.

4. A radiation imaging apparatus as defined in claim 2, wherein:
- the supporting/moving means supports the device in a state in which it is suspended from the ceiling of a room, and moves the device in vertical and horizontal directions.

5. A radiation imaging apparatus as defined in claim 1, wherein:
- the detecting means detects the magnitudes and directions of the external forces which are applied to the operating portion, and outputs detection signals that represent the magnitudes and directions of the external forces; and
- the target values for movement of the device are determined such that the device is moved in the directions in which the external forces are applied at speeds corresponding to the magnitudes of the external forces.

6. A radiation imaging apparatus as defined in claim 2, wherein:
- the detecting means detects the magnitudes and directions of the external forces which are applied to the operating portion, and outputs detection signals that represent the magnitudes and directions of the external forces; and
- the target values for movement of the device are determined such that the device is moved in the directions in which the external forces are applied at speeds corresponding to the magnitudes of the external forces.

7. A radiation imaging apparatus as defined in claim 3, wherein:
- the detecting means detects the magnitudes and directions of the external forces which are applied to the operating portion, and outputs detection signals that represent the magnitudes and directions of the external forces; and
- the target values for movement of the device are determined such that the device is moved in the directions in which the external forces are applied at speeds corresponding to the magnitudes of the external forces.

8. A radiation imaging apparatus as defined in claim 4, wherein:
- the detecting means detects the magnitudes and directions of the external forces which are applied to the operating portion, and outputs detection signals that represent the magnitudes and directions of the external forces; and
- the target values for movement of the device are determined such that the device is moved in the directions in which the external forces are applied at speeds corresponding to the magnitudes of the external forces.

9. A radiation imaging apparatus as defined in claim 1, wherein:
- the unique oscillation component attenuating means attenuates the signal components employing a variable low pass filter.

10. A radiation imaging apparatus as defined in claim 2, wherein:
- the unique oscillation component attenuating means attenuates the signal components employing a variable low pass filter.

11. A radiation imaging apparatus as defined in claim 3, wherein:
- the unique oscillation component attenuating means attenuates the signal components employing a variable low pass filter.

12. A radiation imaging apparatus as defined in claim 5, wherein:
- the unique oscillation component attenuating means attenuates the signal components employing a variable low pass filter.

* * * * *